United States Patent
Austin et al.

[11] Patent Number: 6,090,043
[45] Date of Patent: Jul. 18, 2000

[54] TISSUE RETRACTOR RETENTION BAND

[75] Inventors: Gary Austin, Euclid; J. Timothy Austin, Concord; George J. Picha, Independence, all of Ohio

[73] Assignee: Applied Medical Technology, Inc., Cleveland, Ohio

[21] Appl. No.: 09/313,143

[22] Filed: May 17, 1999

[51] Int. Cl.$^7$ .................................................. A61B 17/02
[52] U.S. Cl. ...................... 600/217; 600/231; 600/233; 128/880
[58] Field of Search ...................... 128/846, 869, 128/870, 876, 877, 878, 879, 880, 882; 600/201, 217, 231, 233, 226; 24/116 A, 300, 301, 265 H

[56] References Cited

U.S. PATENT DOCUMENTS

| | | |
|---|---|---|
| Re. 32,201 | 7/1986 | Scott, Jr. . |
| 2,384,304 | 9/1945 | Helfrick . |
| 2,659,904 | 11/1953 | McGinnis ........................ 128/869 X |
| 2,845,925 | 8/1958 | Jayle . |
| 3,038,468 | 6/1962 | Raeuchle . |
| 3,070,088 | 12/1962 | Brahos . |
| 3,515,129 | 6/1970 | Truhan . |
| 3,522,800 | 8/1970 | Lesser . |
| 3,542,015 | 11/1970 | Steinman . |
| 3,762,401 | 10/1973 | Tupper . |
| 3,823,709 | 7/1974 | McGuire . |
| 3,857,386 | 12/1974 | Ashbell . |
| 3,882,855 | 5/1975 | Schulte et al. . |
| 4,274,398 | 6/1981 | Scott, Jr. . |
| 4,430,991 | 2/1984 | Darnell . |
| 4,434,791 | 3/1984 | Darnell . |
| 4,610,243 | 9/1986 | Ray . |
| 5,174,279 | 12/1992 | Cobo et al. . |
| 5,514,076 | 5/1996 | Ley . |
| 5,638,584 | 6/1997 | De Anfrasio . |
| 5,709,646 | 1/1998 | Lange . |
| 5,769,783 | 6/1998 | Fowler . |
| 5,785,649 | 7/1998 | Fowler, Jr. . |
| 5,899,853 | 5/1999 | Fowler, Jr. . |
| 5,964,697 | 10/1999 | Fowler, Jr. ........................... 600/217 X |
| 5,964,698 | 10/1999 | Fowler ................................... 600/217 |

FOREIGN PATENT DOCUMENTS 32 34 875 A1  3/1984  Germany .

OTHER PUBLICATIONS

A. Kh. Izmailov and B.L. Elyashevich, "Universal Retractor for Cavity Surgery", Jul. 10, 1973, p. 320.

Two and Four FingerStay, Lone Star Medical Products, Inc. (undated).

"Tupper's Universal Handholder and Retractor Set", Accurate Surgical & Scientific Instruments Corporation, p. 39, (undated).

*Primary Examiner*—Jeffrey A. Smith
*Attorney, Agent, or Firm*—Pearne & Gordon LLP

[57] ABSTRACT

A surgical stay including a hook, a handle and an elastomeric band. The hook has a tissue engaging portion and is retained by the handle such that the tissue engaging portion extends from a first end of the handle. A handle end of the band is retained by a second end of the handle. The band has a longitudinal body and at least one hub disposed around the body. The hub has a generally flat engagement surface facing the handle.

21 Claims, 6 Drawing Sheets

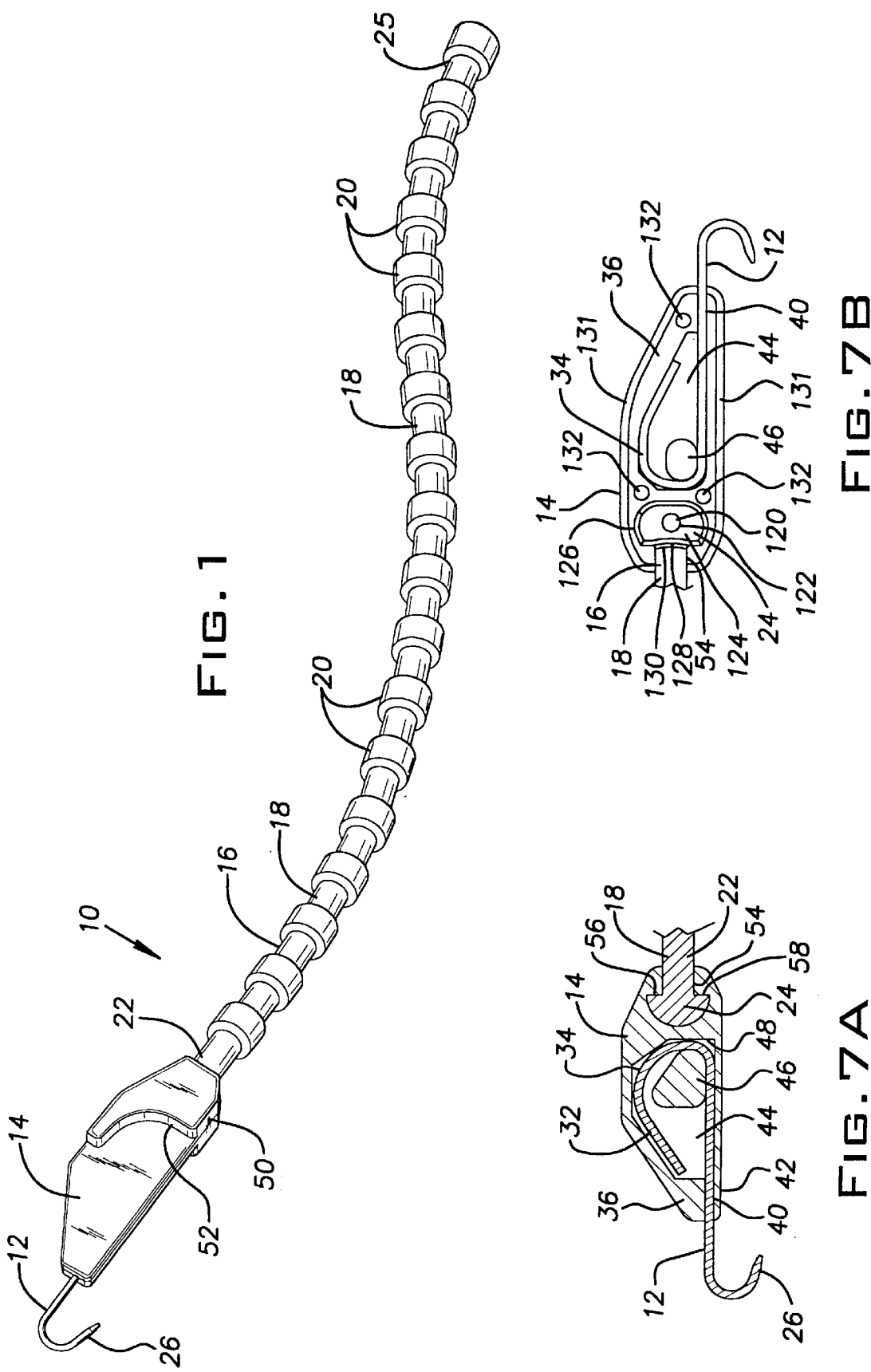

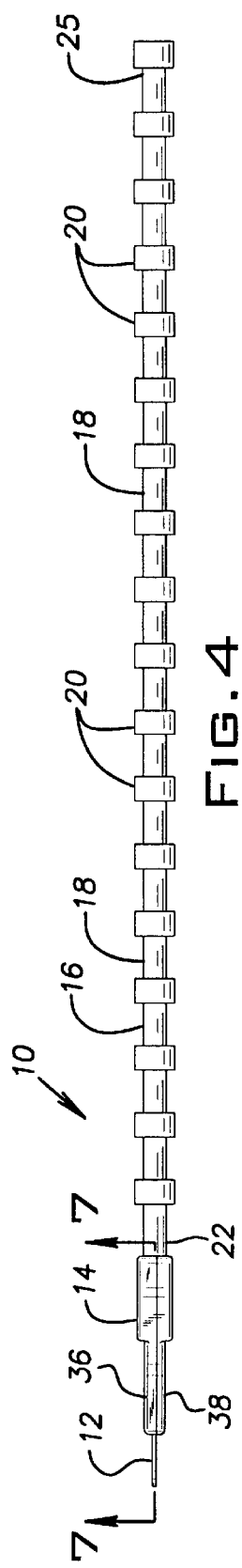
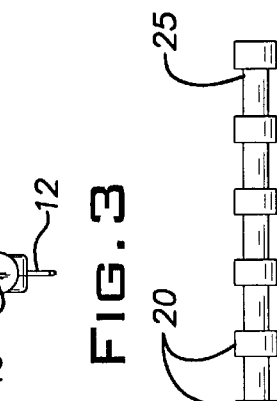
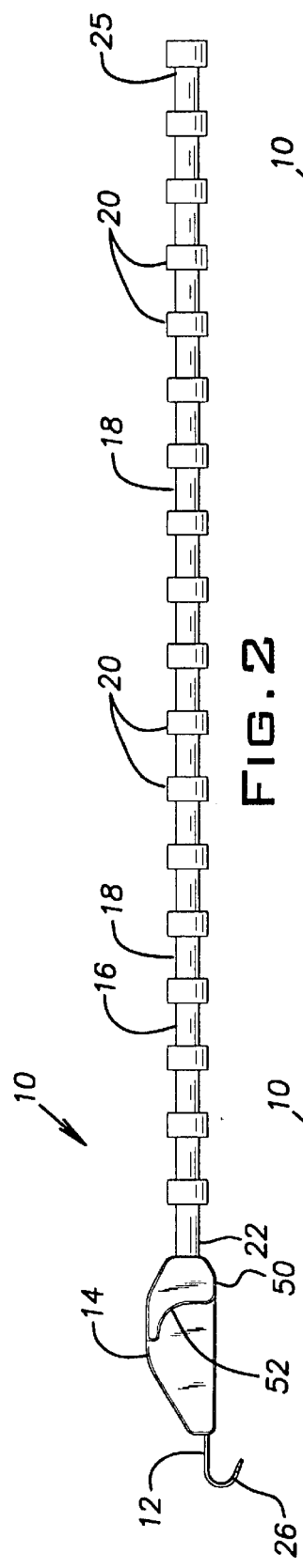
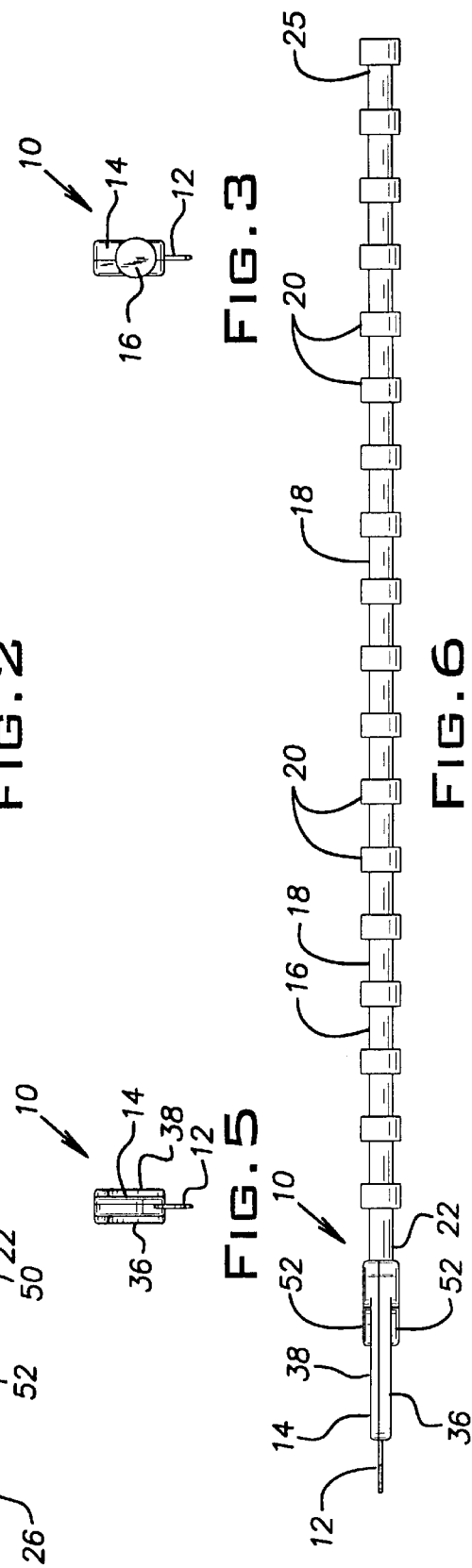

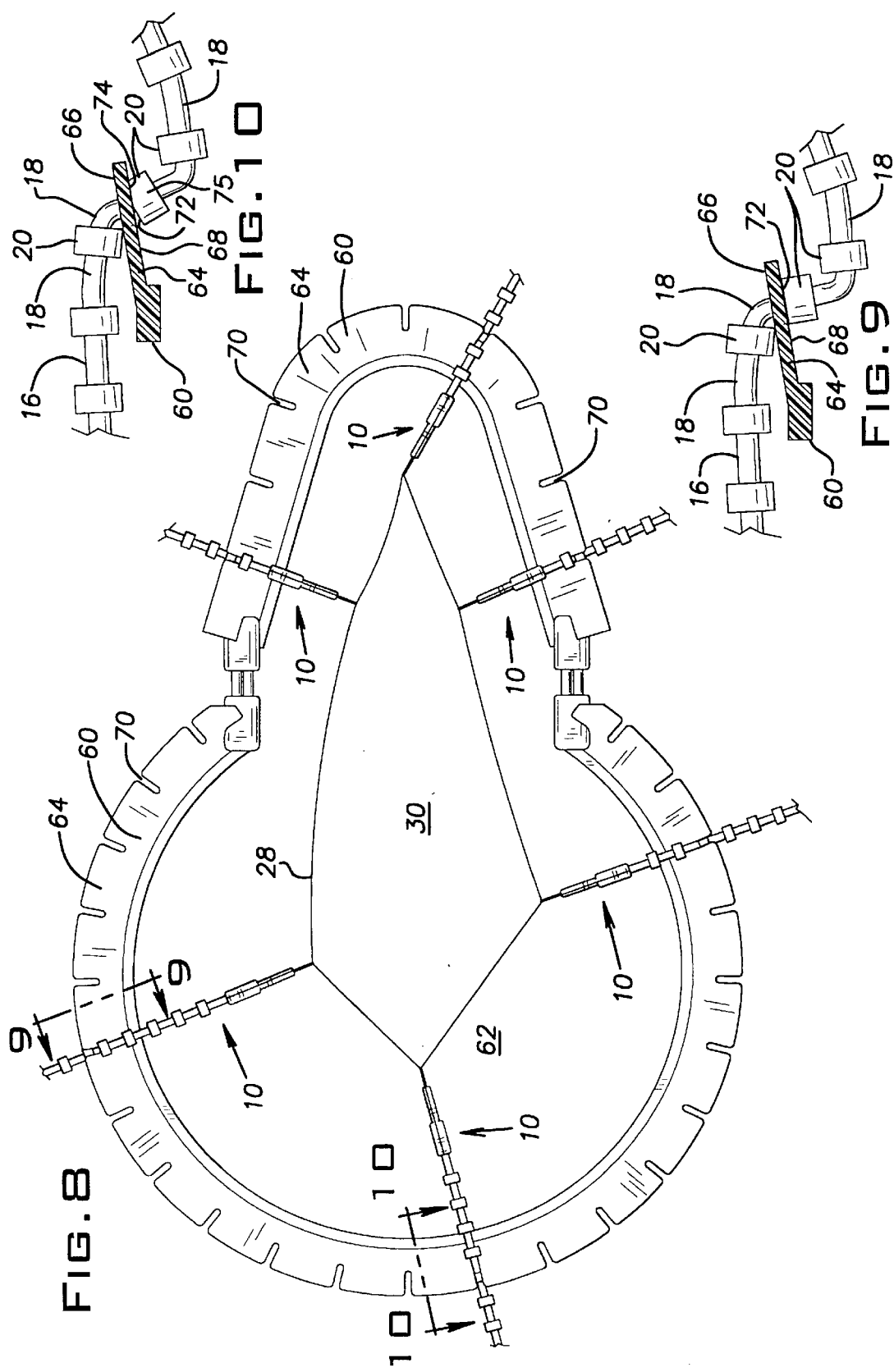

TISSUE RETRACTOR RETENTION BAND

BACKGROUND OF THE INVENTION

1. Field of the Invention

The present invention is directed toward surgical retractor systems and, more specifically to a retractor stay having an elastomeric band.

2. Description of Related Art

It has proven to be desirable in many surgical procedures to provide means to maintain a surgical incision in an open or exposed condition. Several tissue retraction systems have been developed over the years in response to the need for a means to maintain tissue out of the way of the surgeon. One such system includes a frame or support and a tissue-engaging portion.

One type of conventional frame is a frame made from rigid material with a plurality of notches spaced around the frame. The notches are formed to facilitate attachment of a surgical stay. Example surgical frames of this type are illustrated by U.S. Pat. Nos. 5,785,649, 5,769,783, 4,434, 791, 4,430,991, and Re 32,021, the disclosures of which are expressly incorporated herein by reference in their entireties. Additional example frames are disclosed in U.S. patent application Ser. Nos. 09/275,137 filed Mar. 23, 1999, now U.S. Pat. No. 5,951,467, and 29/091,483, filed Jul. 30, 1998, now U.S. Pat. No. D412,576, the disclosures of which are expressly incorporated herein by reference in their entireties and are commonly owned by the assignee of the present application.

Stays for use with such frames are known in the art and generally have a retention hook, a handle and a band. Example stays of this type are illustrated by U.S. Pat. Nos. 5,785,649, 5,769,783, 4,430,991, 3,762,401, and Re 32,021, the disclosures of which are expressly incorporated herein by reference in their entireties. However, these stays suffer from one or more disadvantages. The band of most of these stays is elastomeric and intended to be releasably received by the notches on the frame. The elastomeric bands have either a uniform diameter along their entire length or, as illustrated in FIG. 11, a series of alternating smaller diameter portions and spherically-shaped enlarged diameter sections, or hubs.

The term spherically-shaped hub is not intended to include hub configurations with a concave leading end that engages the frame. Examples of hubs with concave leading edges can be found in U.S. application Ser. Nos. 29/096,289, filed Nov. 9, 1998, now U.S. Pat. No. D414,265, and 29/085,628 filed Mar. 26, 1998, now abandoned, the disclosures of which are expressly incorporated herein by reference in their entireties and are commonly owned by the assignee of the present application.

Elastomeric bands having either a uniform diameter or spherical hubs tend to easily deform and slip through the retractor frame notches, thereby allowing the incision to close. Even though the prior art spherical hubs are larger than the notches in the frame, they tend to slip through the notches since their shapes enable the hubs to leverage themselves through the notch. In addition, the frame and stay tend to become wet during surgery from substances such as blood and irrigation fluid. Although slipping occurs during dry conditions, it occurs with greater frequency during wet conditions since the wetness acts as a lubricant to lower the frictional forces normally retaining the stay in the frame. In addition, many of the prior art stays have handles and bands that contain openings and/or cavities in which blood and debris can collect. Such a stay is not autoclavable or reusable.

It has been found that, depending on the type of tissue and size of the incision, about 0.5 to about 3 pounds of force is required to retract an incision. Under dry conditions, stays having spherical hubs were tested to determine how much force was required to pull the spherical hub through the retractor frame notches. The average force required was 2.78 pounds, with a standard deviation of 0.35. The force required to pull spherical hubs through the frame when wet is even lower.

Other stays have bands made from metal balls held together by metal links protruding through holes formed in the balls. Although metal balls are generally too rigid to pull through frame notches, they are not suitable for autoclaving because debris collects in the holes of the balls. Furthermore, the ball and link type design is less preferred by surgeons who desire the elasticity of elastomeric retractor stay bands. Elastic properties allow the hook and handle of the stay to move with the tissue being retracted as the surgical site moves during the operation. An inelastic stay can easily tear the tissue being retracted. Elastic stays are also easily released from the tissue and frame by stretching the band.

Therefore, there exists a need in the art for an autoclavable, elastic retractor stay that will not inadvertently disengage from or pull through the frame.

There is also a need for a simple to use retractor for resisting the natural tendency of fingers and thumbs to curl during hand and wrist surgery and that does not apply localized pressure to the fingers being restrained. U.S. Pat. No. 3,762,401 discloses a frame having slots through which elastic bands extend. The bands are used to hold the patient's fingers and thumb in place during an operation. However, this arrangement is very cumbersome and difficult to use as bands for each finger must be threaded through the frame, wrapped around each finger, tightened and secured. Other conventional devices for resisting the clenching tendency of fingers have a narrow band or other geometry which have been known to apply localized pressure on the fingers being restrained. This application of localized pressure has the tendency to cause cuts, reduce circulation, and cause other undesirable injury to the patient.

SUMMARY OF THE INVENTION

The present invention overcomes these disadvantages by providing a surgical stay including a hook, a handle and an elastomeric band wherein the band is specially designed to remain engaged with an associated surgical frame and to resist pull forces that may be expected during a surgical procedure. The hook has a tissue engaging portion and is retained by the handle such that the tissue engaging portion extends from a first end of the handle. A handle end of the band is retained by a second end of the handle. The band has a longitudinal body and at least one hub disposed around the body. The hub has a generally flat engagement surface facing the handle.

According to another aspect of the invention, a stay is provided having a broad body disposed between and connecting a first band and a second band.

BRIEF DESCRIPTION OF THE DRAWING

These and further features of the present invention will be apparent with reference to the following description and drawings, wherein:

FIG. 1 is a perspective view of a surgical retention stay according to a first embodiment of the present invention.

FIG. 2 is a front elevational view of the surgical retractor stay according to the first embodiment of the present invention.

FIG. 3 is a right end view of the surgical retractor stay according to the first embodiment of the present invention.

FIG. 4 is a top view of the surgical retractor stay according to the first embodiment of the present invention.

FIG. 5 is a left end view of the surgical retractor stay according to the first embodiment of the present invention.

FIG. 6 is a bottom view of the surgical retractor stay according to the first embodiment of the present invention.

FIG. 7A is a cross-sectional view along the line 7—7 in FIG. 4 illustrating a first handle embodiment of the surgical retractor stay according to the first stay embodiment of the present invention.

FIG. 7B is a partial elevational view of the surgical retractor stay with a second handle body member removed to illustrate a second handle embodiment of the surgical retractor stay according to the first stay embodiment of the present invention.

FIG. 8 is schematic view of a series of surgical retractor stays according to the first embodiment of the present invention in use.

FIG. 9 is a cross-sectional view along the line 9—9 in FIG. 8.

FIG. 10 is a cross-sectional view along the line 10—10 in FIG. 8.

DETAILED DESCRIPTION OF THE INVENTION

Figure 11:
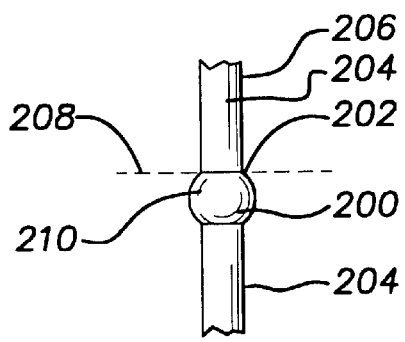
FIG. 11 is a conventional spherical hub for a surgical retractor stay.

In the detailed description which follows, identical components have been given the same reference numeral. In order to clearly and concisely illustrate the present invention, certain features may be shown in somewhat schematic form and the drawings may not necessarily be to scale.

With reference to FIGS. 1 through 8, a surgical retractor stay 10 according to a first embodiment of the present invention is illustrated. The stay 10 includes a retention hook 12, a handle 14 and an elongated elastic member, or band 16. As will be discussed in more detail below, the band 16 has a longitudinal body 18 having a series of hubs 20. A proximal end, or handle end 22, of the band 16 is terminated by a retaining bulb 24 (FIGS. 7A and 7B). A distal end, or free end 25, of the band 16 is located distal to the handle 14.

The hook 12 is preferably made from metal, such as stainless steel. The hook 12 has a first end, or tissue engaging portion 26, extending from the handle 14. The tissue engaging portion 26 is preferably curved, hook shaped, or otherwise bent to grasp tissue 28 surrounding an incision 30 and hold the incision 30 open. As illustrated in FIG. 8, multiple stays 10 can be used in concert with each other to hold the incision 30 open and thereby provide stable access to the incision 30. The hook 12 has a second end 32 which is secured by the handle 14. Preferably, the second end 32 of the hook 12 is bent to form a securing loop 34.

The handle 14 has a first body member 36 and a second body member 38. The first body member 36 and the second body member 38 are adapted to mate together to form the handle 14. The first body member 36 and the second body member 38 are permanently fastened to one another, preferably with adhesive or thermal bonding, and cooperate to capture the second end 32 of the hook, as will be described hereinafter.

As illustrated in FIG. 7A, a first handle embodiment is shown. The first body member 36 is provided with a groove 40 at a first end 42 thereof. The first body member 36 is also provided with an internal recess 44 for accepting the securing loop 34 of the hook 12. The groove 40 securely surrounds the hook 12 as the hook 12 enters the handle 14. The groove 40 forms a passage for the hook 12 to enter the handle 14 so that the securing loop 34 portion of the hook 12 can be received in the recess 44. Accordingly, the recess 44 is in communication with the groove 40. The recess 44 is shaped to accommodate the securing loop 34. Preferably, the first body member 36 has a boss 46 located in the recess 44 and extending through the securing loop 34 of the hook 12 so as to assist in retaining the hook 12 in the handle 14.

The boss 46 is located such that a portion of the hook 12 is trapped between the boss 46 and at least one sidewall 48 of the recess 44. Preferably, the boss 46 is dimensioned so that the second body member 38, which preferably has a flat interior side, flatly engages the boss 46 and the unrecessed portion of the first body member 36, thereby trapping the hook 12 in the handle 14. The first body member 36 is preferably thicker than the second body member 38 in order to have enough room for the groove 40 and recess 44 in which the hook 12 is secured.

As best shown in FIGS. 1 and 2, a second end 50 of the handle 14 is preferably provided with shoulders 52 for assisting in gripping the handle 14 portion of the stay 10. The shoulders 52 project from the exterior side surfaces of the first body member 36 and the second body member 38. Shoulders 52 can optionally be provided at the first end 42 of the handle 14 as well.

With continued reference to FIG. 7A, the second end 50 of the handle 14 is provided with a channel 54 for receiving and retaining the retaining bulb 24 of the band 16. Preferably, portions of the channel 54 are formed in both the first body member 36 and the second body member 38. When the first body member 36 and the second body member 38 are assembled together, thereby forming the channel 54, the channel 54 and retaining bulb 24 have complimentary shapes such that the handle 14 securely traps the bulb 24 in the handle 14 to prevent separation of the handle 14 and band 16. The bulb 24 preferably includes a planar face 56 which is in a generally perpendicular relationship to the longitudinal axis of the body 18 and faces toward the free end 25 of the band 16. The planer face 56 forms an engagement surface which coacts with a complimentary surface 58 in the channel 54 to prevent the band 16 from being pulled from the handle 14. As illustrated in FIG. 7A, the channel 54 and bulb 24 are semi-spherical. However, one skilled in the art will appreciate that bulb 24 and channel 54 can have other shapes so long as they have complementary engaging surfaces to prevent disengagement. Preferably, the first body member 36 and the second body member 38 fit securely around the retaining bulb 24 and body 18 of the band 16. This not only helps to keep the handle 14 and band 16 from disengaging, but also prevents blood and debris from entering the channel 54. Optionally, the first body member 36 and the second body member 38 can slightly compress the portion of the body 18 of the band 16 received in the channel 54 of the handle 14 so as to further prevent disengagement and entry of debris. The shoulders 52 at the second end 50 of the handle 14 not only assist the surgeon or user grip the stay 10, but provides extra thickness to the handle 14 to accommodate the channel 54. Alternative methods of connecting the band 16 and the handle 14 are contemplated. These methods include for example, increasing the hardness of the handle end 22 of the band 16 and/or fashioning a clipped type of engagement between the band 16 and the handle 14.

With reference to FIG. 7B, a second, and more preferred, embodiment of the handle 14 is illustrated. FIG. 7B shows the interior side of the first body member 36, the hook 12 and a portion of the band. For clarity, the second body member 38 has been removed. As in the first handle embodiment, the first body member 36 is provided with the groove 40, the recess 44 and the boss 46 for receiving and trapping the hook 12.

As in the first handle embodiment, the second end 50 of the handle 14 is provided with a channel 54 to receive and retain the retaining bulb 24 of the band 16. However, in the second embodiment of the handle 14, the first body member 36 is provided with a peg 120 located in the channel 54. The peg 120 extends into a hole 122 defined by the bulb 24. The peg 120 and the hole 122 are preferably arranged transverse to the longitudinal axis of the band 16. In the second handle embodiment, the corresponding shapes of the bulb 24 and channel 54 are not as critical as in the first handle embodiment. This is because the peg 120 will assist in retaining the band 16. In the second handle embodiment, the bulb 24 preferably has a more oval shape with flattened side surfaces 124. The shape gives the bulb 24 a trimmer size to better fit in the handle 14. Edges 126 of the bulb 24 are preferably provided with rounded corners. An intersection 128 between the bulb 24 and the body 18 of the band 16 is preferably molded with a fillet 130. The fillet 130 serves to relieve stresses caused when the band 16 is placed under tension thereby helping to avoid tearing of the band at the intersection 128. The term fillet, as used herein, is understood to means a rounded inside corner. More specifically, a fillet is a concavely curved section at the angle formed by the junction of two surfaces.

The first body member 36 of the second handle embodiment is preferably provided with a perimeter notch 131 adapted to receive a perimeter projection provided on the second body member 38. The first body member 36 is also preferably provided with receptacles 132 for receiving posts provided on the second body member 38. One skilled in the art will appreciate that the foregoing features can be switched between the first and second body members 36, 38. The second body member 38 can also be provided with a receptacle for receiving the peg 120, depending on the length of the peg 120. Alternatively, both the first and second body members 36, 38 can be provided with pegs which are received in the hole 122 or multiple holes 122 defined by the bulb 24.

The second handle embodiment is preferably provided with shoulders 52 to assist in gripping the handle 14. In either handle embodiment, the handle 14 has a pair of body members 36, 38 which connect together and retain the band 16 and the hook 12. Preferably, the band 16 and the hook 12 are retained independently of one another. More specifically, the band 16 plays no role in retaining the hook 12 and the hook 12 plays no role in retaining the band 16. The band 16 and hook 12 preferably do not contact each other.

With additional reference to FIGS. 8 through 10, a frame 60 is adapted to surround all or part of a surgical site 62 and act as a support for the stay 10, or series of stays 10, so that the stay(s) 10 can hold the incision 30 open. It is noted that frames of this type are well known in the art and do not form part of the present invention. If further information regarding surgical frames is desired, reference should be made to the surgical frame patents and applications identified in the Description of Related Art section of this specification. Accordingly, the frame 60 is only illustrated and described to the extend necessary to understand the present invention. The frame 60 has a flange 64 having an upper surface 66 and a lower surface 68. The upper surface 66 and the lower surface 68 are generally planar. The frame 60 is provided with notches 70 extending from the upper surface 66 to the lower surface 68. The notches 70 are adapted to releasably receive the body 18 of the band 16. The notch 70 is preferably sized about as large as the body 18 of the band 16, sometimes smaller. Should the notch 70 be sized smaller than the body 18 of the band 16, the frame 60 will slightly compress the body 18 as the body 18 is inserted into the notch 70.

The stay 10 is used by placing the tissue engaging portion 26 of the hook 12 on the tissue 28 to be retained and inserting the body 18 of the band 16 in one of the notches 70 of the frame 60. The stay 10 is prevented from moving forward, or towards the surgical site 62, and from being pulled through the notch 70 by mechanical interference. More specifically, the hub 20 adjacent the frame 60 abuts a portion of the lower surface 68 of the frame 60 surrounding the notch 70 thereby preventing movement of the stay 10 except for stretching of the elastic band 16.

The band 16 is preferably solid and made from elastomeric material, such as silicone rubber. The band 16 preferably has a durometer hardness of about 40 Shore A. As should be apparent, a higher hardness will increase the engagement properties between the hubs 20 and the frame 60. However, this will sacrifice the elastic qualities of the stay 10. This is not desirable since a relatively less elastic stay 10 will loose characteristics important to most surgeons, namely the ability of the hook 12 and handle 14 portions of the stay 10 to move with the tissue 28 being retained as the surgical site 62 shifts during the operation to minimize tearing of the tissue 28 being retracted. The elastic characteristics also allow the stay 10 to be removed from the tissue 28 and/or the frame 60, and allow the band 16 to conveniently bend as best illustrated in FIGS. 9 and 10.

Figure 12:
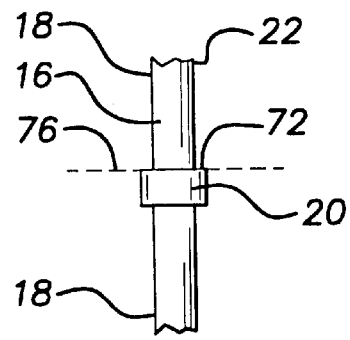
FIGS. 12 through 16 are views of hub embodiments for surgical retractor stays according to the present invention.

With additional reference to FIG. 12, disposed around the body 18 of the band 16 are a plurality of hubs 20 which are spaced apart along the length of the body 18. The hubs 20 extend radially from the body 18. Preferably, the entire band 16, including the hubs 20, the body 18 and the retaining bulb 24, is integrally molded in a single molding process. More preferably, the band 16 is liquid injection molded. Each hub 20 is provided with a frame engagement surface 72 at an end of the hub 20 facing the surgical site 62. Preferably, the frame engagement surface 72 is an annular flat face disposed in a generally perpendicular relationship to the longitudinal axis of the body 18. Another way to describe the band 16 is an alternating series of cylindrical body portions and larger cylindrical hub 20 portions. No matter how the band 16 is described, it is important to recognize that the hubs 20 are provided with a broad, or planar, engagement surface 72 to contact the lower surface 68 of the flange 64 portion of the frame 60 surrounding the notch 70. The engagement surface 72 is effective to distribute tension placed on the band away from the body 18 of the band 16 and thus away from the lower surface 68 area immediately adjacent the notch 70.

With spherical hubs 200 (FIG. 11), as taught by the prior art, the hub 200 initially makes a line contact with the frame 60 at a leading edge 202 of the hub 200 which circles the body 204 on an end of the hub 200 closest to the handle end 206. Consequently, tension is transferred from the hub 200 to the frame 60 immediately adjacent the body 204 which corresponds to an area on the frame 60 that is right against the notch 70. This transfer of force so close to the notch 70 allows the leading edge 202 of the spherical hub 200 to start entering the notch 70. Once partially entered into the notch 70, the spherical hub 200 compresses and squeezes through the notch 70. A merger plane 208 where the body 204 and the hub 200 interface to create the leading edge 202 is shown by a broken line. Merger plane 208 is perpendicular to the longitudinal axis of the body 204. A curved or arcuate surface 210 of the hub 200 extends from the merger plane 208 away from the handle end 206 of the body 204. As more tension is placed on the body 204, the arcuate surface 210 is pulled towards the frame 60 and becomes the engagement surface of the hub, albeit an engagement surface that tends to pull through the notch 70. The surface 210 is disposed further away from the handle end 206 than the merger plane 208 is from the handle end 206.

As illustrated in FIG. 9, the hub 20 of the present invention has an engagement surface 72 that is in face-to-face contact with the lower surface 68 of the frame 60. This engagement provides a distributed area where any tension placed on the band 16 will be transferred to the frame 60. This distributed area is larger than, and therefore capable of absorbing greater amounts of tension than, the line-type contact made between the lower surface 68 of the frame 60 and a spherical hub 200 enabling the spherical hub 200 to leverage and compress its way through the notch 70.

As illustrated in FIG. 10, the band 16 is placed under relatively less tension than the band 16 in FIG. 9. Therefore, the engagement surface 72 of the hub 20 will have a tendency to sit askew against the lower surface 68 of the frame 60 such that only a portion 74 of the engagement surface 72 is in engagement with the lower surface 68. The hub 20 will also have a tendency to compress due tension placed on the elastomeric qualities of the band 16 resulting in the configuration illustrated. Nevertheless, the portion 74 of the engagement surface 72 that does contact the lower surface 68 is in a flat relationship with, and makes face-to-face contact with, the lower surface 68. Therefore, the forces placed on the band 16 are distributed over a broad area which is capable of absorbing greater amounts of tension than the contact area made between a spherical hub and the lower surface 68 of the frame 60. It should be noted that although the hub 20 shown in FIG. 10 is deformed, a side 75 of the hub 20 is not in contact with the frame 60. Rather, only the portion 74 of the engagement surface 72 which is in contact with the lower surface 68 of the frame 60. This is a result of the elastomeric qualities of the band 16 and the flange 64 portion of the frame 60 being placed at an angle. When greater tension is placed on the band 16, the body 18 of the band 16 will have a tendency to be pulled further into the notch 70 and the hub 20 will have a tendency to be drawn into tighter engagement with the lower surface 68 of the frame 60, resulting the arrangement shown in FIG. 9.

Under dry conditions, stays 10 having hubs 20 with flat engagement surfaces 72 were tested to determine how much force was required to pull the hub 20 through the notches 70 of the retractor frame 60. None of the hubs 20 pulled through the notches 70. Rather, the bands 16 broke at an average force of 8.76 pounds, with a standard deviation of 0.16. This is significantly higher than the force of about 0.5 to about 3 pounds required to retract tissue and is therefore adequate to prevent the hub 20 from slipping through the notch 70 during a surgical procedure. Wet conditions should not significantly change the foregoing test results since wetness will not change the breaking point of the band 16. Nor will wetness be effective as a lubricant to reduce the amount of force required to pull the hub 20 through the frame 60 since the hub 20 engages the frame 60 in a face to face relationship. More specifically, mechanical interference over a relatively large surface area holds the hub 20 in place relative to the frame 60. The hub 20 of the present invention does not have an engagement end that is easily leveraged through the notch 70 that would be assisted by lubrication. Therefore, the present invention provides a retractor stay 10 having the engagement qualities of a metal band and the elastic qualities of an elastomeric band.

Referring now to FIG. 12, a portion of the stay 10 according to the present invention is illustrated. The body 18 and the hub 20 merge with each other at an end of the hub 20 adjacent a merger plane 76, shown in FIG. 12 by a broken line. The merger plane 76 is generally perpendicular to the longitudinal axis of the band 16. The engagement surface 72 of the hub 20 is at least as close to the handle end 22 of the band 16 as merger plane 76 is to the handle end 22. Most preferably, the engagement surface 72 is coincident with the merger plane 76. It should also be understood that the circular cross-sectional shape of the illustrated hub 20 is exemplary. The present invention is not to be limited to a stay 10 having the illustrated shapes. Other suitable shapes include, for example, oval and rectangular. In these alternative examples of cross-sectional shapes, the engagement surface 72 will not be annular. However, so long as the engagement surface 72 flatly mates against the frame 60, the hubs 20 will still be effective to prevent the hub 20 from pulling through the frame 60.

Figure 13:
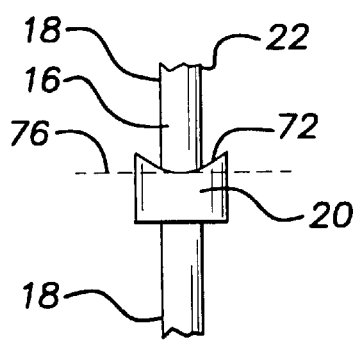
Figure 14:
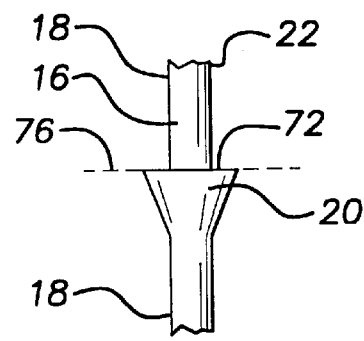
Figure 15:
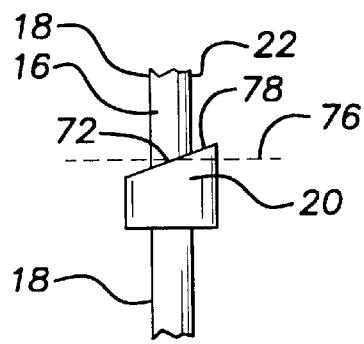

Referring now to FIGS. 13–15, example alternative embodiments of hubs 20 according to the present invention are illustrated. Referring to FIG. 13, the hub 20 is provided with an engagement surface 72 that is not planar or flat but is still effective to distribute tension placed on the band away from the lower surface 68 area immediately adjacent the notch 70. The engagement surface 72 is at least as close to the handle end 22 of the band as the merger plane 76 is to the handle end 22. Example shapes are a bowl-shaped engagement surface 72 and the illustrated concave engagement surface 72 where the merger plane 76 is tangent the engagement surface 72. Under tension, the concave shape may deform against the frame 60 to be relative planar, but the force applied to the band 16 will remain distributed away from the body 18 of the band 16 and away from the notch 70.

Referring to FIG. 14, the hub 20 can be conical hubs 20 or semi-spherical, similar to the retaining bulb 24 illustrated in FIG. 7A, but with the face 56 side facing the surgical site 62 and serving as the engagement surface 72. In this embodiment, the engagement surface 72 is at least as close to the handle end 22 of the band 16 as the merger plane 76 is to the handle end 22. Illustrated in FIG. 14 is a conical hub 20 having a planar engagement surface 72 coincident with the merger plane 76. This type of hub 20 has the ability to be pulled through the frame 60 in one direction to add tension to the band 16 thereby further retracting the tissue 28, but will not inadvertently pull through the frame 60 towards the surgical site 62.

Referring to FIG. 15, another alternative embodiment of the present invention is illustrated. In this embodiment the engagement surface 72 is angled or beveled with respect to the longitudinal axis of the band 16 to match an angled flange 64 portion of the frame 60 (FIGS. 9 and 10). In this embodiment, the engagement surface 72 is no longer generally perpendicular to the longitudinal axis of the band 16, but the engagement surface 72 still flatly mates against the lower surface 68 of frame 60. The hub 20 mates with the body 18 at a merger plane 76 such that a portion 78 of the engagement surface 72 is at least as close to the handle end 22 of the band 16 as the merger plane 76 is to the handle end 22.

Figure 16:
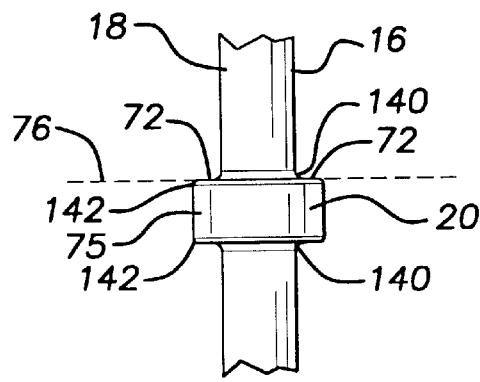

Referring to FIG. 16, a most preferred embodiment of the hub 20 is illustrated. In this embodiment, the merger plane 76 is coincident with the engagement surface 72. The band 16 is preferably molded with a fillet 140 at an intersection of the body 18 and the engagement surface 72. Referring to the definition of the term fillet recited above, the fillet 140 is a concavely curved section located at the junction of the surface forming the side of the body 18 and the generally planar engagement surface 72. The radius of the fillet 140 is preferably about 0.010 inches. The fillet 140 acts to locally reduce stress placed on the band 16 when it is placed under tension. Reducing the stress at the intersection of the body 18 and the hub 20 reduces the likelihood that the band 16 will break at this intersection.

Although the fillet 140 is disposed closer to the handle end 22 of the band 16 than the merger plane 76 and/or the engagement surface 72, the fillet is too small to have any significant engagement with the frame 60. The fillet 140 will most likely enter the notch 70 when the band 16 is placed under tension. The engagement surface 72 will still make face-to-face contact with the lower surface 68 of the frame 60. The engagement surface 72 will provide a distributed area to transfer any tension placed on the band 16 to the frame 60. The fillet 140 is too small with respect to the engagement surface 72 to allow the hub 20 to start to enter the notch 70, and compress and leverage its ways through the notch 70. This is why the merger plane 76 is considered to still be coincident with the engagement surface 72 in this hub embodiment rather than positioned at another point relative to the fillet 140.

The hub 20 is also preferably provided with a rounded corner 142 at the intersection of the engagement surface 72 and the side 75 of the hub 20. The radius of the rounded corner 142 is preferably about 0.005 inches. The rounded corner 142 is provided to impart a softer texture to the band 16 and also eases release of the band 16 from the mold.

Figure 17:
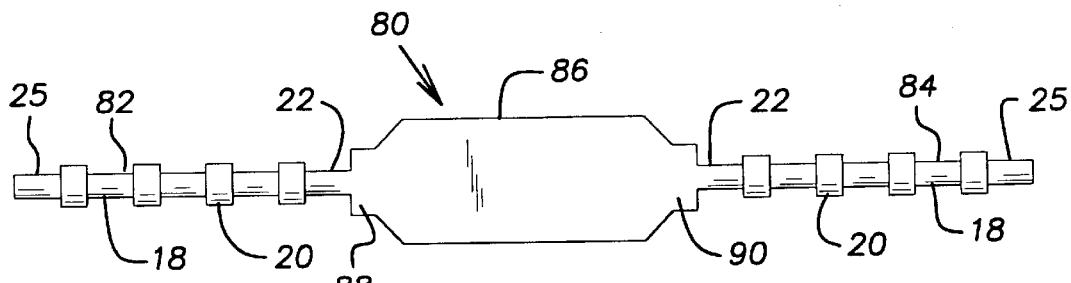
FIG. 17 is a surgical retractor stay according to a second embodiment of the present invention.
Figure 18:
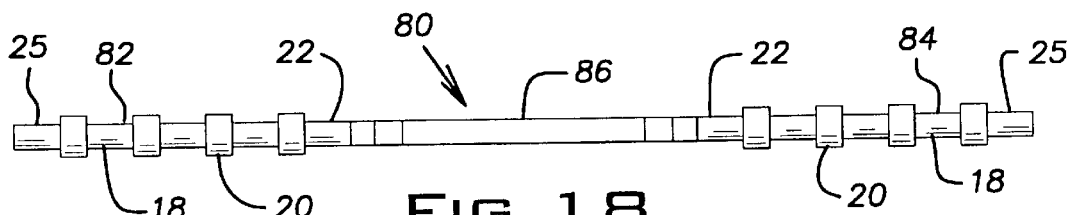
FIG. 18 is a side view of the surgical retractor stay according to the second embodiment of the present invention.

Referring to FIGS. 17 and 18, a surgical retractor stay, or strap 80, according to a second embodiment of the present invention is illustrated. The strap 80 provides a first band 82, a second band 84 and a broad body 86, such as a planar strip. The first band 82 and the second band 84 of the second embodiment are similar to the band 16 of the first embodiment and have a body 18, a series of hubs 20, a proximal end 22 and a free end 25. The broad body 86 has a first end 88 and a second end 90. The broad body 86 is disposed between and connected to the first band 82 and the second band 84. More specifically, the first end 90 is connected to the proximal end 22 of the first band 82 and the second end 90 is connected to the proximal end of the second band 84. As with the band 16 of the first embodiment, the entire strap 80 is preferably a unitary piece of elastomeric material such that the first band 82, the second band 84, and the broad body 86 are integrally connected and stretchable. Such a strap 80 can be made of materials such as silicone rubber, PVC or polyurethane, or a combination thereof. To impart desired retention characteristics, the hardness (durometer) of the strap 80 can be increased or decreased relative to the hardness of the first and second bands 82, 84.

Alternatively, the broad body 86 can be made of a different material than the first and second bands 82, 84. Example materials are foam or a woven fabric. Preferably, the material is stretchable. In the case where the broad body 86 is a different material than the first and second bands 82, 84, a mechanical connection will be required to secure the parts together. Example connectors include the bulb/channel arrangement used by the first embodiment between the band 16 and the handle 14, snaps, clips, stitching and the like.

Figure 21:
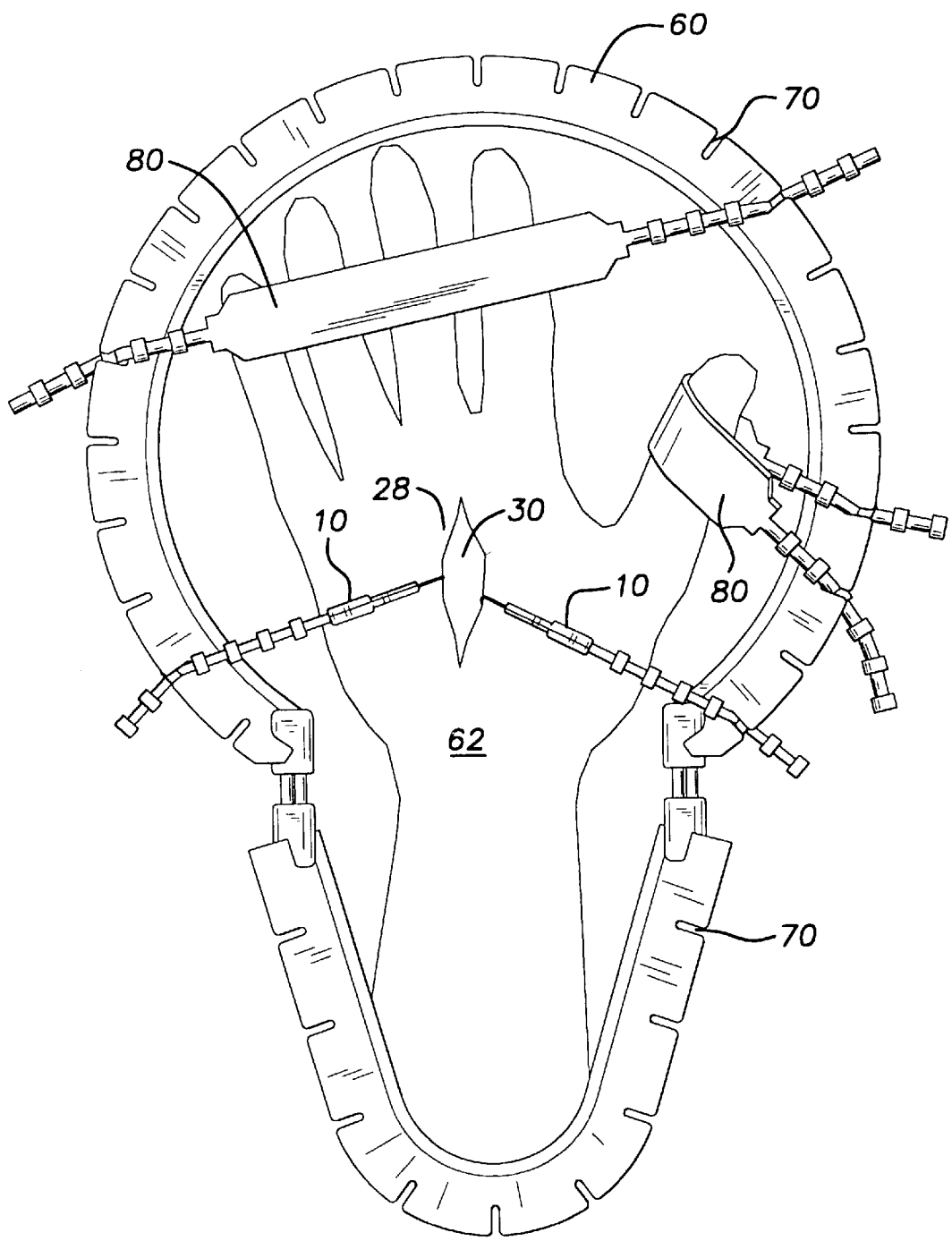
FIG. 21 is a schematic view of surgical stays according to the first and second embodiments of the present invention in use.

FIG. 21 depicts a pair of straps 80 in use with a frame 60 and two stays 10 of the first embodiment during a surgical procedure on the palm or wrist of a hand. One of the straps 80 is used to hold the patient's fingers down by resisting the fingers' tendency to curl by natural tension of the flextured tendons. As shown, the first band 82 is held by a notch 70 on one side of the frame 60. The second band 84 is held by another notch 70 on the opposite side of the frame. The broad body 86 portion of the strap 80 lies on top of the patient's fingers to offer resistance against the fingers.

The thumb also has a tendency to curl during palm and wrist surgery. The other strap 80 illustrated in FIG. 21 is used to hold back the patient's thumb. The first and second bands 82, 84 are placed in separate notches 70 adjacent the thumb and the broad body 86 portion is wrapped around the thumb as illustrated to resist inward movement of the thumb. Alternatively, both bands 82, 84 may be placed in the same notch 70, if the notch 70 is sized appropriately. Fingers can also be held away from one another by using the strap 80 in the same manner as illustrated for the thumb.

Figure 19:
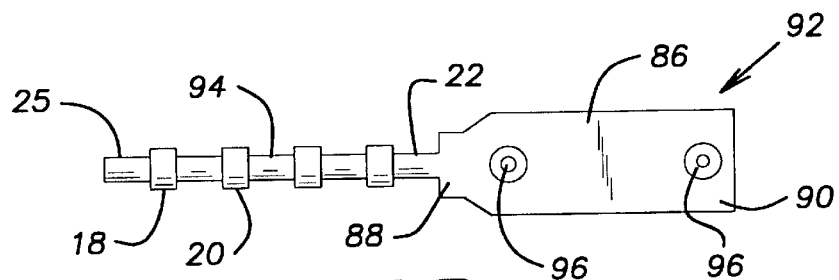
FIG. 19 is a surgical retractor stay according to a third embodiment of the present invention.

Referring to FIG. 19, a surgical retractor stay, or strap 92, according to a third embodiment of the present invention is illustrated. The strap 82 provides a band 94 similar to that of the band 16 of the first embodiment and a broad body 86 similar to the broad body 86 of the second embodiment. The proximal end 22 of the band 94 is connected to the first end 88 of the broad body 86. Since the broad body 86 is made of flexible material, it is adapted to bend so as to form a loop when the first end 88 is fastened to the second end 90. The fastening can be by any mechanical fastening means. The fastening means can be preattached to the strap 92 or attached to the strap 92 as needed. The illustrated example of fastening means are snaps 96 provided at end 88, 90 of the broad body 86, that are adapted to mate together. Other fastening means examples include hook and loop type fasteners, clips, crimps, threaded devices, buckles, buttons and the like. The ends 88, 90 can also be fastened by fusing them together or with adhesive. The strap 92 can alternatively be provided with a fastening means including a hole and a serrated end adapted to fit through the hole without pulling back through, similar to the arrangement of a cable tie or a garbage bag tie.

Figure 20:
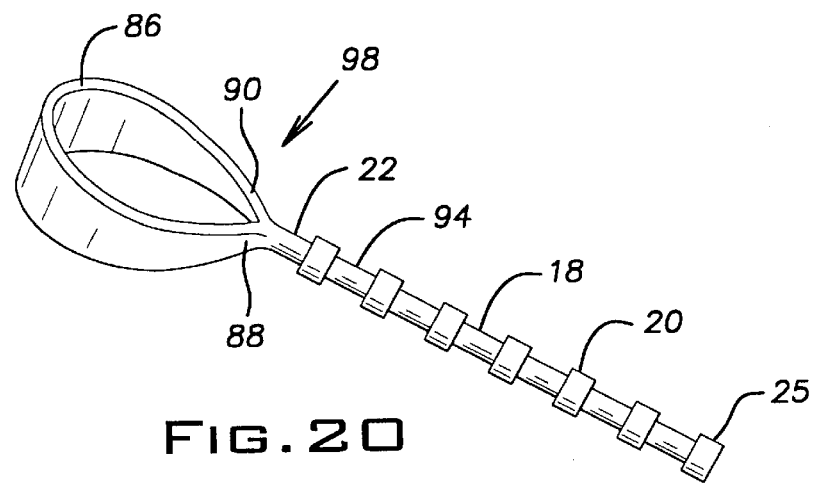
FIG. 20 is a surgical retractor stay according to a forth embodiment of the present invention.

Referring to FIG. 20, a surgical retractor stay, or strap 98, according to a forth embodiment of the present invention is illustrated. The strap 98 is provided with a band 94 similar to the band 16 of the first embodiment. The strap 98 is also provided with a broad body 86 similar to broad body 86 of the second and third embodiments, but both the first end 88 and the second end 90 are permanently connected to the proximate end 22 of the band 94. The connection among the ends 20, 88, 90 is preferably made during the molding process. Alternatively, the strap 92 of the third embodiment can be manufactured and then the second end 90 can be fused or secured with adhesive to the area where the proximal end 22 and the first end 88 connect.

Although particular embodiments of the invention have been described in detail, it is understood that the invention is not limited correspondingly in scope, but includes all changes and modifications coming within the spirit and terms of the claims appended hereto.

What is claimed is:

1. A surgical stay comprising a hook, a handle and an elastomeric band, the hook having a tissue engaging portion, the hook being retained by the handle such that the tissue engaging portion extends from a first end of the handle and a proximal end of the band being retained by a second end of the handle, the band having a longitudinal body and at least one hub disposed around the body, the hub having a generally flat engagement surface facing the handle.

2. The stay according to claim 1, wherein the engagement surface is adapted to make planar contact with a frame.

3. The stay according to claim 1, wherein the engagement surface is generally perpendicular to a longitudinal axis of the band.

4. The stay according to claim 1, wherein the body of the band and the hub are integrally molded.

5. The stay according to claim 1, wherein the handle includes a first member and a second member, the first member and the second member being adapted to mate together to independently retain the hook and the proximal end of the band.

6. The stay according to claim 5, wherein the band is provided with a retaining bulb at the proximal end of the band, the retaining bulb being trapped by the first and second handle members.

7. The stay according to claim 5, wherein the band defines a hole at the proximal end of the band and the first handle member is provided with a pin, the pin extending into the hole.

8. A band for a surgical stay comprising, an elastomeric longitudinal body having a proximal end and a distal end, and at least one hub disposed at a position between the proximal and distal ends of the body and extending radially from the body, the body and hub merging with one another at a location adjacent an engagement surface of the hub, said location defining a merger plane, the merger plane being transverse relative to a longitudinal axis of the body, said engagement surface being at least as close to the proximal end of the body as the merger plane.

9. The elastomeric band for a surgical stay according to claim 8, wherein the engagement surface is planar and is coincident with the merger plane.

10. The elastomeric band for a surgical stay according to claim 8, wherein the engagement surface is concave and faces the proximal end, the merger plane being tangent to the engagement surface.

11. The elastomeric band for a surgical stay according to claim 8, wherein the proximal end of the band is connected to a handle and hook assembly.

12. The elastomeric band for a surgical stay according to claim 8, further comprising a second longitudinal body having a proximal end and a distal end, and at least one hub disposed at a position between the proximal and distal ends of the second body and extending radially from the second body, and a broad body having a first end and a second end, the first end connected to the proximal end of the first longitudinal body and the second end connected to the proximal end of the second longitudinal body such that the broad body is disposed between the first and second longitudinal bodies.

13. The elastomeric band for a surgical stay according to claim 8, wherein the proximal end of the longitudinal body is connected to a broad body.

14. The elastomeric band for a surgical stay according to claim 13, wherein the broad body is elastomeric and integrally formed with the longitudinal body.

15. The elastomeric band for a surgical stay according to claim 13, wherein the broad body has a first end and a second end, and the first end and the second end are adapted to be fastened together.

16. The elastomeric band for a surgical stay according to claim 13, wherein the broad body has a first end and a second end, and the first end and the second end are connected to the proximal end of the longitudinal body.

17. A band for a surgical stay comprising, an elastomeric longitudinal body having a proximal end and a distal end, and at least one hub disposed at a position between the proximal and distal ends of the body and extending radially from the body, the body and hub merging with one another at a location adjacent an engagement surface of the hub, said location defining a merger plane, said merger plane being transverse relative to a longitudinal axis of the body, and at least a portion of the engagement surface being closer to the proximal end of the body than the merger plane.

18. A surgical stay comprising a first elastomeric band, a second elastomeric band and a broad body, each band having a longitudinal body with a proximal end and a distal end and at least one hub disposed around the longitudinal body, each hub having a generally flat engagement surface facing the proximal end of the respective longitudinal body the hub is disposed around, and the broad body having a first end and a second end, the proximal end of the first band connected to the first end of the broad body and the proximal end of the second band connected to the second end of the broad body.

19. A surgical stay comprising a hook, a handle and an elastomeric band, the handle having a first member and a second member, the first member and the second member being adapted to mate together to independently retain the hook and a proximal end of the band, wherein the band is provided with a retaining bulb at the proximal end of the band, the retaining bulb being trapped by the first and second handle members.

20. A surgical stay comprising a hook, a handle and an elastomeric band, the handle having a first member and a second member, the first member and the second member being adapted to mate together to independently retain the hook and a proximal end of the band, wherein the band defines a hole at the proximal end of the band and the first handle member is provided with a pin, the pin extending into the hole.

21. A surgical stay comprising a hook, a handle and an elastomeric band, the handle having a first member and a second member, the first member and the second member being adapted to mate together to independently retain the hook and a proximal end of the band, wherein the hook has a tissue engaging portion and a securing loop, the hook being retained by the handle such that the tissue engaging portion extends from the handle and the securing loop is trapped by the first and second handle members.

* * * * *